United States Patent [19]
Franetzki et al.

[11] Patent Number: 4,511,355
[45] Date of Patent: Apr. 16, 1985

[54] INFUSION DEVICE INTENDED FOR IMPLANTATION IN A LIVING BODY

[75] Inventors: Manfred Franetzki, Uttenreuth; Karl Prestele, Erlangen, both of Fed. Rep. of Germany

[73] Assignee: Siemens Aktiengesellschaft, Berlin & Munich, Fed. Rep. of Germany

[21] Appl. No.: 418,525

[22] Filed: Sep. 15, 1982

[30] Foreign Application Priority Data

Sep. 25, 1981 [DE] Fed. Rep. of Germany ....... 3138320

[51] Int. Cl.³ .............................................. A61M 5/14
[52] U.S. Cl. .................................. 604/131; 604/153; 604/891; 128/DIG. 12
[58] Field of Search ................................ 128/DIG. 12; 604/890–892, 49, 93, 131, 151, 153, 126

[56]  References Cited

U.S. PATENT DOCUMENTS

| | | |
|---|---|---|
| 3,647,117 | 3/1972 | Hargest . |
| 3,765,414 | 10/1973 | Arlen . |
| 4,013,074 | 3/1977 | Siposs . |
| 4,041,944 | 8/1977 | Rhodes ...................... 128/DIG. 12 |
| 4,191,181 | 3/1980 | Franetzki et al. .......... 128/DIG. 12 |
| 4,217,894 | 8/1980 | Franetzki ............................ 604/131 |
| 4,398,908 | 8/1983 | Siposs ........................ 128/DIG. 12 |

FOREIGN PATENT DOCUMENTS 0019817 12/1980 European Pat. Off. .
1918684 10/1970 Fed. Rep. of Germany .

Primary Examiner—C. Fred Rosenbaum
Assistant Examiner—Michelle N. Lester
Attorney, Agent, or Firm—Hill, Van Santen, Steadman & Simpson

[57]  ABSTRACT

The exemplary embodiments relate to a device housing implantable in the body and having a reservoir for the infusion of fluid and having a conveying and dosing unit for conveying the fluid from the reservoir to the discharge opening of a discharge catheter. In known devices of this type, the reservoir is held at a reference pressure which is lower in comparison to the pressure at the fluid discharge location in order, in case of a defect, to prevent fluid from flowing out. According to the present disclosure, pressure equalization between the inside space of the housing and the environment is effected for example by a hydrophobic or hydrophilic diaphragm with pores of a specific size or a diffusion diaphragm in combination with a pressure control valve in the wall of the device housing.

22 Claims, 6 Drawing Figures

INFUSION DEVICE INTENDED FOR IMPLANTATION IN A LIVING BODY

BACKGROUND OF THE INVENTION

The invention relates to an infusion device intended for implantation in a living body, said infusion device being comprised of a device housing implantable in the patient's body having a reservoir for infusion fluid and having a conveying and dosing unit for conveying the fluid from the reservoir to the discharge opening of a catheter.

An infusion device of the type initially cited is known, for example, from the U.S. Pat. No. 4,191,181. For safety reasons the infusion fluid in the reservoir of the device is kept under a pressure which is lower than the pressure at the discharge opening of the catheter. Such a measure prevents fluid from discharging out of the reservoir into the patient's body due to a leak in the capsule or pump. In order to execute this measure, for example, a flexible fluid reservoir is charged by a vapor pressure of such a substance as has a corresponding pressure at body temperature. It is also possible to fill a buffered gas into the tightly encapsulated device housing under such a pressure that, taking the gas equation into consideration, an under-pressure in comparison to the pressure of the environment is still maintained even given a full fluid reservoir.

A hermetic encapsulation of the device housing given maintenance of under-pressure over longer times, however, also produces a series of problems. For example, temperature fluctuations and external changes of air pressure which can change the pressure differential between the body tissues and the inside of the housing must be taken into consideration. As a result, one must proceed from a relatively great under-pressure, for example up to 0.5 bar. The consequence of this, however, specifically given employment of roller pumps as the conveying and dosing unit, is that the danger of a reflux of fluid in the catheter exists during disengagement of the successive pump rollers from the fluid conveyor tube.

SUMMARY OF THE INVENTION

It is therefore an object of the invention to create a device of the type initially cited with safety features such as make the maintenance of under-pressure in the device housing unnecessary.

This object is inventively achieved in that means for balancing the pressure between the inside space of the housing and the environment are allocated to the device housing.

The environment can both be the tissue surrounding the implanted infusion device and the environment outside of the body. The point of departure is that the pressure in the body tissue or, respectively, in the body fluid largely corresponds to the external barometric pressure.

The pressure equalization in the invention ensues over a gas-permeable or fluid-permeable diaphragm. Such a diaphragm can consist of hydrophobic material with pores of a specific size given which only gas is passed through; the diaphragm, however, can also consist of a fine-pore, hydrophilic material so that the pressure equalization is accomplished by an exchange of body fluid.

In a preferred realization of the invention, a high permeability diffusion diaphragm can also be employed, particularly in conjunction with a pressure control valve. Thereby, given a slow emptying of the reservoir, a matching of the pressure inside the housing to the external pressure can be achieved solely by means of gas diffusion, whereas an immediate pressure compensation of the inside of the housing and the environment in the body tissue is effected by the valve during percutaneous re-filling of infusion fluid. By so doing, a build-up of excess pressure in the device housing is avoided. In a simplest embodiment, such a valve can consist of an elastic stopper which closes an opening and provides a ventilation channel in the housing wall.

Instead of the valve, it is also possible to briefly produce a connection of the inside of the housing with the environment outside of the patient's body over a special paracentesis septum. This, however, is only required given re-filling of infusion fluid and does not negatively influence the inventive pressure equilibrium given a long-time application of the implanted infusion device.

In an advantageous development of the invention, the diaphragm for pressure equalization can be a part of the device housing, for example the diaphragm can also directly form the housing wall; however, it can also be connected via a tube to the inside of the housing or, respectively, can itself be designed tube-like, so that it can be placed at a suitable location in the patient's body.

A device for supplying medications to the human or animal body has already been proposed in the U.S. Pat. No. 4,217,894 in which a diaphragm is introduced in the housing wall. Thereby, however, that diaphragm is to have specific, hydrophilic properties in order to be able to suction bodily fluid quantitatively in by means of a conveying and dosing unit in order to be able to dissolve a solid medication therein. As a result of the suctioning of bodily fluid for the purpose of dissolving solid medications, however, a completely different situation arises wherein, in particular, the storage of medications as infusion fluid as well as problems connected with emptying and/or re-filling fluid are to be avoided. In this regard, thus, there are no points of contact with the present invention.

Further advantages and details of the invention derive from the following figure description of exemplary embodiments with reference to the accompanying drawing sheets; and other objects, features and advantages will be apparent from this detailed disclosure and from the appended claims.

DETAILED DESCRIPTION

Figure 1:
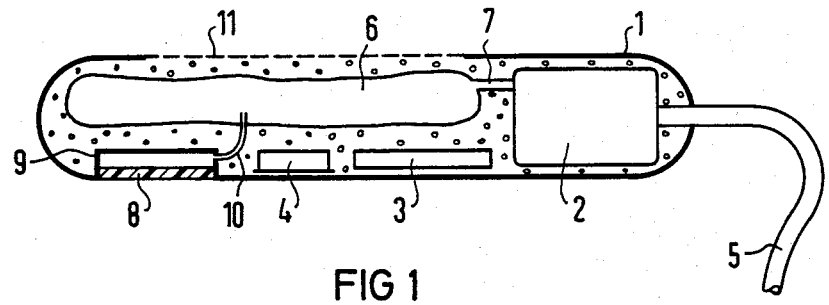
FIGS. 1 through 5 show in a highly schematic illustration variously constructed infusion devices in cross-section.

In FIG. 1, reference numeral 1 indicates a device housing of an implantable infusion device. As a flat capsule, this is a three-dimensional shape roughly equivalent to the housing of a heart pacemaker and is formed of implantable material compatible with body tissue, for example titanium. A conveying and dosing unit 2, a unit 3 with electronic circuits for the drive and control of the conveying and dosing unit 2, and an energy supply unit 4 (battery) are indicated in the device housing 1; 5 indicates a catheter which can be placed at a suitable location inside the patient's body. 6 indicates a reservoir for infusion fluid.

Insulin, for example, can be percutaneously introduced as infusion fluid into the reservoir 6 over a re-filling septum 8 introduced into the device housing and having a connecting line 10. To this end, the re-filling septum 8 consists of a self-sealing elastomer which can be punctured with a standard injection cannula.

The reservoir 6 for the fluid is protected against damage during re-filling of infusion fluid by means of a so-called needle stopper 9. A conveying wick can be situated within the reservoir 6, the fluid being suctioned off bubble-free over a conveyor tube 7 to the discharge catheter 5 from said wick by means of the conveying and dosing unit 2.

In this regard, the structure of an infusion device is known from the prior art. Where the known infusion devices are hermetically encapsulated for the purpose of maintaining under-pressure in the device housing, a diaphragm 11 is now inserted to form part of the wall of the device housing 1.

In the embodiment according to FIG. 1, the diaphragm 11 consists of hydrophobic material with pores which are so fine that, even given the maximum pressure differential between the housing interior and the environment, no body fluid is allowed to pass through the pores. The same also applies to body cells and/or bateria. To this end, standard hydrophobic filters such as frits or diaphragm filters can be employed which, for example, consist of polyolefins, PTFE or of similar materials.

With such a design of the infusion device, it is guaranteed that, given a continuous fluid discharge from the reservoir, the gas dissolved in the surrounding body tissue or in the body fluids can enter into the device housing. As a result, a pressure equalization is largely seen to. Since the gas pressure in the body tissue or, respectively, in the body fluid approximately corresponds to the external air pressure, a matching to the barometric pressure of the environment is likewise guaranteed.

Given transcutaneous re-filling of the reservoir, it is expedient to first always suction the remaining content of fluid in the reservoir out. Given such a comparatively fast operation, practically no gas from the environment of the device housing can diffuse-in so that an under-pressure can briefly arise. Given the immediately following re-filling of the reservoir, the gas present in the device housing is displaced into the surrounding body tissue and is absorbed there. It can be expedient to suction off a device-external gas bubble which may potentially arise.

Figure 2:
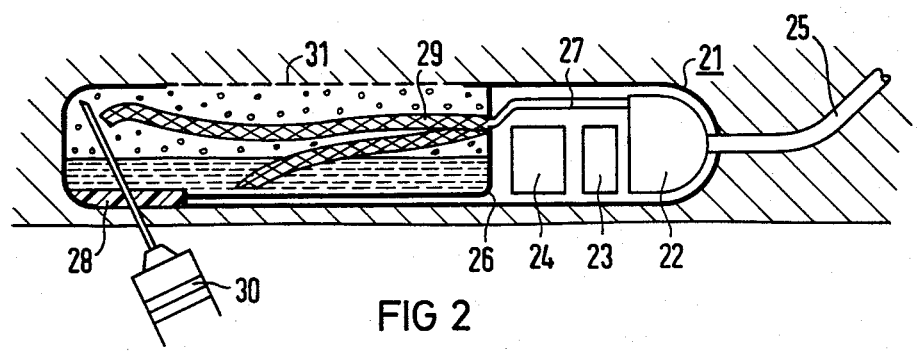

In FIG. 2, the reference numerals 21 through 28 as well as 31 correspond in their sequence to the reference numerals of FIG. 1 increased by twenty. Specifically indicated with 29 is a suction wick in the reservoir. In the embodiment according to FIG. 2, the reservoir 26 is rigidly designed for containing the infusion fluid. This has the advantage that a part of the reservoir 26 simultaneously forms the housing wall and that the re-filling septum 28 can lead directly into the reservoir 26. Thereby, the needle stopper is advantageously directly integrated in the housing wall. Certain structural simplifications also derive. A syringe for percutaneous sucking or, respectively, re-filling of the infusion fluid through the indicated body tissue is referenced with 30.

In this exemplary embodiment, the diaphragm 31 directly closes off the reservoir 26 with infusion fluid from the body tissue. No leakage of fluids can be permitted, so that the hydrophobia of the diaphragm 31 is an unconditional prerequisite.

Given this embodiment of the invention, the pressure equalization ensues by means of direct gas exchange between the environment and the reservoir 26. For this reason, the bubble-free sucking of fluid by the conveying and dosing unit 22 is to be guaranteed by means of the wick 29. Further, it must also be seen to that the conveyor wick 29 is in contact with infusion fluid given all filling conditions of the reservoir 26 and given every possible patient position.

Figure 3:
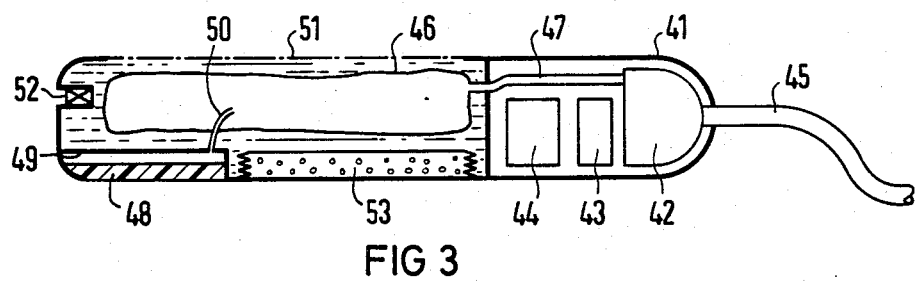

In the infusion device of FIG. 3, the sequence of reference numerals 41 to 51 again represent units corresponding to those in FIG. 1; in accord with FIG. 1, a flexible fluid reservoir 46 is provided. According to this embodiment of the invention, the diaphragm 51 which is introduced in the housing wall of the device housing 41 consists of fine-pore, hydrophilic material so that low-molecular body fluids can proceed through the pores. The pore size of the diaphragm 51 is selected in such manner that larger fluid molecules and, in particular, body cells and/or bacteria as well are arrested.

In this embodiment, the pressure equalization is achieved solely by means of the exchange of body fluid. Before the transcutaneous re-filling of the infusion fluid, medication residues are again to be suctioned out via the re-filling septum 48 with a syringe. To that end, a buffer volume with a compressible agent, i.e., a gas, must exist in the device housing 41. Expediently, a separate, flexible bellows 53 with a gas contained therein is provided, said bellows matching to the respectively existing volume. Likewise, the elastic container of the bellows 53 can also contain a liquid or some other substance with a vapor pressure which is lower than the external barometric pressure and, thus, guarantees a volume-dependent pressure.

Given the embodiment of FIG. 3, the thickness, area and the material of the hydrophilic diaphragm 51 are selected in such manner that the diaphragm has a relatively low flow resistance. By so doing, no significant under-pressure arises in the reservoir 46 even given the maximum pump rate of the conveying and dosing unit 42. Fabric or fiber strengthened hydrogels, for example, are suitable as materials for the diaphragm 51. In order to quickly remove the excess body fluid from the inside space of the housing 41 and to re-introduce it into the body tissue during transcutaneous re-filling of the reservoir 46 with infusion fluid, a valve 52 is additionally provided in the housing, said valve opening given over-pressure in the inside of the housing and letting the fluid out.

Figure 4:
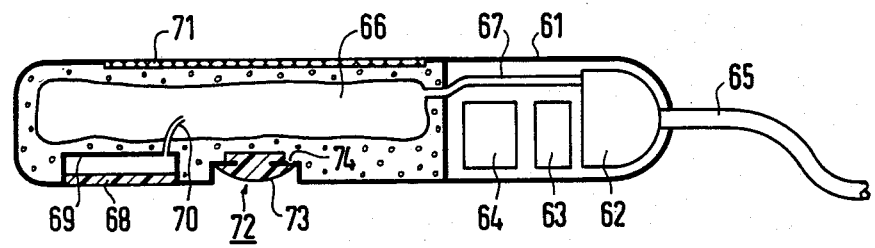

The exemplary embodiment according to FIG. 4 is fundamentally constructed in accord with FIG. 3, whereby corresponding units derive in the numerical sequence of 61 through 71. A so-called diffusion diaphragm 71 having a high permeability for gases is specifically provided here as the diaphragm, consisting, for example, of silicone. The pressure equalization between the inside of the housing and the environment given this embodiment of the invention, thus, ensues solely by means of diffusion, this completely sufficing given the usual, slow emptying of the reservoir as a result of the micro-dosing by the conveying and dosing unit 62. Since a diffusion-determined rate of gas exchange does not suffice during re-filling, a valve 72 is again additionally provided. As a result, a significantly faster escape of the gas from the device housing 1 in comparison to the diffusion rate is possible given percutaneous re-filling of the reservoir 66. It is also possible as an alternative to a valve, that an elastic diffusion diaphragm of such nature is employed which bulges toward the outside until the excess pressue has been dismantled by diffusion.

The valve 72 can consist of a rubber plug 73 in the wall of the device housing 61 which plug 73 covers an opening 74 in the housing wall and tightly closes it under normal pressure but opens given excess pressure in the inside of the housing.

Figure 5:
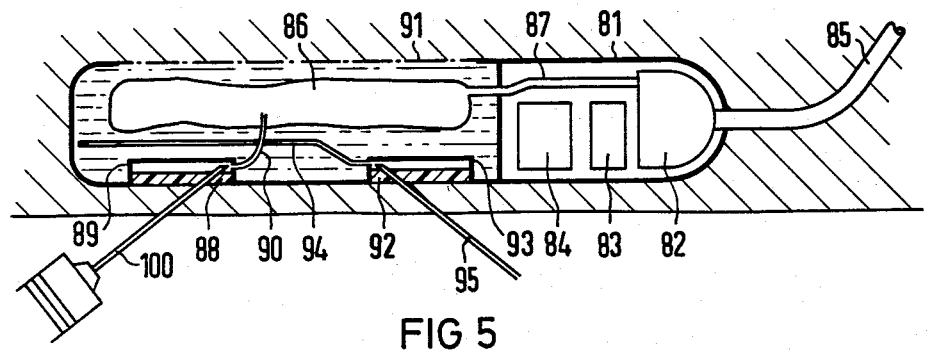

In FIG. 5, the reference numerals 81 through 91 denote the units described on the basis of the preceding figures in a corresponding numerical sequence. Given this embodiment of the invention, a gas-permeable or fluid-permeable diaphragm can be facultatively employed as the diaphragm 91. In addition to the fluid re-filling septum 88, a further septum 92 is provided as a separate paracentesis system which again consists of a self-sealing elastomer with following needle stopper 93. An internal tube 94 is conducted from the septum 92 to the lowest location of the housing.

Given the infusion device according to FIG. 5, the pressure equalization during the slow conveying operation and emptying of the reservoir 86 by the conveying and dosing unit 82 ensues over the gas-permeable or fluid-permeable diaphragm in accord with the exemplary embodiments described above. Now, however, the pressure or, respectively, volume equalization in the percutaneous re-filling of the reservoir does not ensue by means of gas or fluid exchange with the surrounding body tissue but, rather, with the environment outside of the patient's body. Such an equalization can be particularly quickly accomplished; at the same time, the substances temporarily collected in the device housing are removed.

For the re-filling operation, thus, a cannula 95 is tapped into the second septum 92, said cannula 95 leading through the tissue toward the outside. Particularly given employment of the hydrophilic diaphragm, this has the advantage that the body fluid is not expressed from the inside of the housing into the body but, rather, can flow off toward the outside. For the embodiment having the gas-permeable diaphragm, however, the second septum 92 is expediently disposed in such manner that condensed water or other body fluids which may have penetrated can be directly sucked off from the lowest housing parts with paracentesis cannula.

Figure 6:
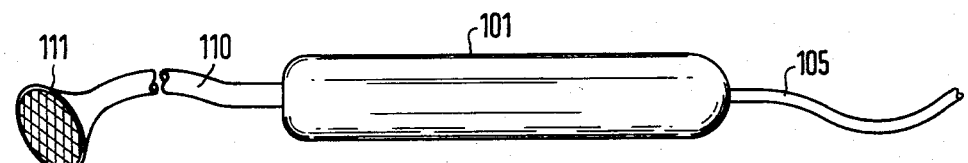
FIG. 6 schematically illustrates an external view of an infusion device representing a further embodiment of the invention.

The further access to the inside of the capsule present in FIG. 6 also has additional advantages in the manufacture and encapsulation of the overall infusion device.

Given the infusion devices according to FIGS. 1, 3, as well as 4 and 6, a flexible reservoir for the infusion fluid is respectively provided in the device housing. In the normal case, the fluid is filled into the reservoir bubble-free through the septum by means of a cannula or, respectively, syringe. However, it can also be useful given these embodiments to provide an additional suction wick in accord with FIG. 2 in order to safely guarantee a bubble-free pumping of the fluid even given gas bubbles which may potentially exist.

In the preceding FIGURES, the respective, differently designed diaphragms 11, 31, 51, 71 and 91 were always illustrated as a part of the housing wall. However, it can be expedient to connect such a diaphragm to the device housing via an additional tube; this can be of significance particularly given a pressure equalization by means of exchanging body fluid.

In FIG. 6, a correspondingly designed device housing with catheter 105 as well as a tube 110 with terminating diaphragm 111 is referenced with 101. Thereby, the tube 110 discharges at its proximal end in the corresponding chamber of the device housing 101 and is selected of such length that it can be placed in patient's body up to a reservoir of body fluid. The tube 110 can itself consist of diaphragm material.

The inventive diffusion devices described on the basis of the various exemplary embodiments can particularly be employed as an artificial pancreas for administering insulin in diabetes therapy. Thereby, considerable problems in the implantation of such devices into a living body are overcome with the invention. The pressure equalization between the inside space of the housing and the environment of the housing is respectively accomplished in that, during operation of the implanted diffusion device, the infused fluid is replaced by body gases or by body fluid as well. Thereby, the flexible reservoir in FIGS. 1, 3, 4 and 5 respectively encloses the entire infusion fluid not visibly illustrated), while the space not filled by the infusion fluid in the rigid reservoir in FIG. 2 is filled up by body gases.

A reliable aspiration of infusion fluid is always guaranteed as a result of the above features independently of the filling condition of the reservoir even given changing spatial attitudes of the infusion device due to changes of position of the patient's body. The additional disposition of a pressure control valve in the housing wall particularly serves for the equalization of excess pressures occurring relatively briefly, for example in an airplane or when filling the reservoir.

It will be apparent that many modifications and variations may be made without departing from the scope of the teachings and concepts of the present invention.

We claim as our invention:
1. An infusion device for implantation in a patient's body, comprising
  a protective housing;
  a flexible walled reservoir positioned within said housing, formed of a fluid impermeable material and adapted to contain an infusion liquid therein;
  a conveying and dosing unit positioned within said housing for conveying said infusion liquid from said reservoir to a catheter discharge opening; and
  means communicable with the interior of said reservoir for permitting refilling of said reservoir from exterior of said housing;
  said protective housing having means providing communication between the interior of said housing exteriorly of said reservoir and bodily fluids exterior of said housing.
2. An infusion device according to claim 1, with said means providing communication between the interior of said housing exteriorly of said reservoir and bodily fluids exterior of said housing, comprising a gas permeable diaphragm for providing pressure equalization during operation of said conveying and dosing unit.
3. An infusion device according to claim 1, with said means providing communication between the interior of said housing exteriorly of said reservoir and bodily fluids exterior of said housing, comprising a diaphragm which is part of said housing and which provides said communication.
4. An infusion device according to claim 1, with said means providing communication between the interior of said housing exteriorly of said reservoir and bodily fluids exterior of said housing, comprising a tube ex- tending from the housing having a gas permeable means which can be placed at a suitable location in the patient's body.

5. An infusion device according to claim 1, with said means providing communication between the interior of said housing exteriorly of said reservoir and bodily fluids exterior of said housing, comprising pressure equalization means operable for substantially equalizing pressure between the interior of said housing exteriorly of said reservoir and bodily fluids exteriorly of said housing during conveying of infusion liquid from said reservoir by said conveying and dosing unit, and further comprising a pressure control valve, for equalization of excess pressures at the interior of said housing exteriorly of said reservoir which excess pressures occur relatively briefly.

6. An infusion device according to claim 1, with said means providing communication between the interior of said housing exteriorly of said reservoir and bodily fluids exterior of said housing comprising pressure equalization means operable for substantially equalizing pressure between the interior of said housing exteriorly of said reservoir and bodily fluids exteriorly of said housing during conveying of infusion liquid from said reservoir by said conveying and dosing unit, said means communicable with the interior of said reservoir comprising a first paracentesis means, and said housing having a second paracentesis means connected with the interior of said housing exteriorly of said reservoir and serving for pressure equalization during refilling of said reservoir via said first paracentesis means.

7. An infusion device according to claim 1, with said means providing communication between the interior of said housing exteriorly of said reservoir and bodily fluids exterior of said housing, comprising a gas permeable diaphragm providing communication between the interior of said housing exteriorly of said reservoir and gases dissolved in the body exterior of said housing.

8. An infusion device according to claim 7, with said diaphragm being comprised of hydrophobic material and having pores of a specific size.

9. An infusion device according to claim 1, with said means providing communication between the interior of said housing exteriorly of said reservoir and bodily fluids exterior of said housing, comprising a diffusion diaphragm having high gas permeability.

10. An infusion device according to claim 1, with said means providing communication between the interior of said housing exteriorly of said reservoir and bodily fluids exterior of said housing, comprising a hydrophobic diaphragm having pores of size such that, given the maximum pressure differential between the interior of said housing exteriorly of said reservoir and the body exterior of said housing, no body liquid as well as no body cells and/or bacteria can pass.

11. An infusion device according to claim 1, with said means providing communication between the interior of said housing exteriorly of said reservoir and bodily fluids exterior of said housing, comprising a liquid permeable diaphragm.

12. An infusion device according to claim 11, with said diaphragm being comprised of hydrophilic material and having pores of a specific size.

13. An infusion device according to claim 1, with said means providing communication between the interior of said housing exteriorly of said reservoir and bodily fluids exterior of said housing, comprising a hydrophilic membrane whose pores are of size such that no body cells and/or bacteria can pass through.

14. An infusion device according to claim 1, with said means providing communication between the interior of said housing exteriorly of said reservoir and bodily fluids exterior of said housing, comprising a hydrophilic diaphragm formed of a material which is a fiber strengthened hydrogel.

15. An infusion device according to claim 1, with said means providing communication between the interior of said housing exteriorly of said reservoir and bodily fluids exterior of said housing, comprising a liquid permeable diaphragm for substantially equalizing pressure at the interior of said housing exteriorly of said reservoir with pressure at the exterior of said housing during operation of said conveying and dosing unit, said housing having an expandable container for containing a buffer gas.

16. An infusion device according to claim 1, with said means providing communication between the interior of said housing exteriorly of said reservoir and bodily fluids exterior of said housing, comprising a liquid permeable diaphragm for substantially equalizing pressure at the interior of said housing exteriorly of said reservoir with pressure at the exterior of said housing during operation of said conveying and dosing unit, said housing having an expandable container, said container having a liquid therein with a vapor pressure lower than the external barometric pressure.

17. An infusion device according to claim 1, with said housing having a chamber at the interior thereof and exteriorly of said reservoir, said means providing communication between the interior of said housing exteriorly of said reservoir and bodily fluids exterior of said housing, comprising a liquid permeable diaphragm for supplying body fluid to the chamber for effecting pressure equalization during conveying of infusion liquid from the reservoir, and said housing having a liquid flow control value for letting off body fluid from the chamber in the event of a transitory excess pressure.

18. An infusion device according to claim 1, with said means providing communication between the interior of said housing exteriorly of said reservoir and bodily fluids exterior of said housing, comprising pressure equalization means operable for substantially equalizing pressure between the interior of said housing exteriorly of said reservoir and bodily fluids exteriorly of said housing during conveying of infusion liquid from said reservoir by said conveying and dosing unit, and further comprising a pressure control value for the equalization of excess pressures occurring relatively briefly, said housing having a flow channel therein, and said pressure control value comprising a silicone rubber plug sealing the flow channel.

19. An infusion device for implantation in a patient's body, comprising
 (a) a device housing implantable in the patient's body,
 (b) a reservoir contained in said device housing for storing an infusion liquid therein, said reservoir comprising flexible reservoir wall means formed of essentially fluid impermeable material and having an outer space within said device housing exteriorly of said reservoir wall means,
 (c) conveying and dosing unit contained in said device housing for conveying said infusion liquid from said reservoir to a catheter discharge opening, and (d) refilling means for refilling said reservoir with said infusion liquid from outside of said housing, (e) said device housing having pressure equalization means providing gaseous communication between the exterior of said device housing and the outer space of said reservoir within said device housing, said pressure equalization means thereby providing for pressure equalization between the outer space of said reservoir within said device housing and the outer environment of said device housing.

20. The infusion device according to claim 19, wherein said pressure equalization means comprises a gas-permeable diaphragm.

21. The infusion device according to claim 20, with said gas-permeable diaphragm being part of said device housing.

22. An infusion device for implantation in a patient's body, comprising
- a flexible walled reservoir formed of a fluid impermeable material adapted to contain an infusion liquid therein;
- a conveying and dosing unit in fluid communication with the interior of said reservoir for conveying said infusion liquid from said reservoir to a catheter discharge opening;
- an implanted protective housing implanted in the patient's body and containing said conveying and dosing unit and said flexible walled reservoir therein, with the exterior of said flexible walled reservoir being exposed to the pressure of an interior space of said housing such that said flexible walled reservoir is constricted in volume by an excess pressure in said interior space of said housing over the pressure interiorly of the reservoir,
- said housing having pressure equalization means transmissive of gaseous media but non-transmissive for liquid media providing gaseous communication between said interior space of said housing and gaseous media in the patient's body at the exterior of said housing such that the pressure in said interior space and thus the pressure interiorly of said reservoir is substantially equivalent to the pressure of ambient atmosphere external to the patient's body during operation of said conveying and dosing unit thereby to prevent an underpressure interiorly of the reservoir relative to atmospheric pressure.

* * * * *